United States Patent
Griffiths et al.

(10) Patent No.: US 11,485,016 B2
(45) Date of Patent: **\*Nov. 1, 2022**

(54) SYSTEM AND METHOD FOR COLLISION AVOIDANCE USING VIRTUAL BOUNDARIES

(71) Applicant: INTUITIVE SURGICAL OPERATIONS, INC., Sunnyvale, CA (US)

(72) Inventors: Paul G. Griffiths, Santa Clara, CA (US); Nitish Swarup, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 16/896,083

(22) Filed: Jun. 8, 2020

(65) Prior Publication Data

US 2020/0298406 A1 Sep. 24, 2020

Related U.S. Application Data

(63) Continuation of application No. 16/079,970, filed as application No. PCT/US2017/016427 on Feb. 3, 2017, now Pat. No. 10,717,194.

(Continued)

(51) Int. Cl.
*B25J 9/00* (2006.01)
*B25J 9/16* (2006.01)
(Continued)

(52) U.S. Cl.
CPC ............ *B25J 9/1666* (2013.01); *A61B 34/30* (2016.02); *A61B 34/32* (2016.02); *A61B 34/35* (2016.02);
(Continued)

(58) Field of Classification Search
CPC ........ A61B 2034/102; A61B 2034/105; A61B 2090/3983; A61B 2034/305; A61B 34/71;
(Continued)

(56) References Cited

U.S. PATENT DOCUMENTS 7,607,440 B2 10/2009 Coste-Maniere et al.
8,004,229 B2 8/2011 Nowlin et al.
(Continued)

FOREIGN PATENT DOCUMENTS

JP 2013129018 A 7/2013
WO WO-2013181503 A1 12/2013
(Continued)

OTHER PUBLICATIONS

Extended European Search Report for Application No. EP17756974.6 dated Aug. 22, 2019, 13 pages.
(Continued)

*Primary Examiner* — Ian Jen
(74) *Attorney, Agent, or Firm* — Artegis Law Group, LLP (57) ABSTRACT

A system and method of collision avoidance includes determining a position and an orientation, the position and the orientation being of a repositionable arm or of an instrument, the repositionable arm being configured to support the instrument; determining, based on the position and the orientation, a plurality of first virtual boundaries around the repositionable arm or the instrument; determining a second virtual boundary around an object; determining a first overlap force on the repositionable arm due to a first overlap between the second virtual boundary and a virtual boundary of the plurality of first virtual boundaries; determining a tip force on a distal end of the instrument based on the first overlap force; and applying the tip force as a first feedback force on the instrument or the repositionable arm.

20 Claims, 4 Drawing Sheets

Related U.S. Application Data (60) Provisional application No. 62/300,706, filed on Feb. 26, 2016.

(51) Int. Cl.
| | |
|---|---|
| *A61B 34/00* | (2016.01) |
| *A61B 34/30* | (2016.01) |
| *G16H 50/50* | (2018.01) |
| *A61B 34/32* | (2016.01) |
| *A61B 34/35* | (2016.01) |
| *A61B 90/00* | (2016.01) |
| *A61B 34/20* | (2016.01) |
| *A61B 34/10* | (2016.01) |

(52) U.S. Cl.
CPC ............ *A61B 34/76* (2016.02); *B25J 9/1676* (2013.01); *G16H 50/50* (2018.01); *A61B 34/10* (2016.02); *A61B 34/20* (2016.02); *A61B 2034/2055* (2016.02); *A61B 2034/2061* (2016.02); *A61B 2090/065* (2016.02); *A61B 2090/066* (2016.02); *G05B 2219/40339* (2013.01); *G05B 2219/40492* (2013.01)

(58) Field of Classification Search
CPC . A61B 34/37; A61B 2034/2048; A61B 34/70; A61B 2034/2051; A61B 90/361; A61B 2034/108; A61B 2017/00119; A61B 2034/207; A61B 2034/2072; A61B 34/74; A61B 17/1764; A61B 2017/1602; A61B 90/11; A61B 17/1622; A61B 17/3423
See application file for complete search history.

(56) References Cited

U.S. PATENT DOCUMENTS

| | | | |
|---|---|---|---|
| 8,170,716 B2 | 5/2012 | Coste-Maniere et al. | |
| 8,184,773 B2 | 5/2012 | Cheng et al. | |
| 8,541,970 B2 | 9/2013 | Nowlin et al. | |
| 8,554,368 B2 | 10/2013 | Fielding et al. | |
| 8,571,710 B2 | 10/2013 | Coste-Maniere et al. | |
| 8,624,537 B2 | 1/2014 | Nowlin et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,880,145 B2 | 11/2014 | Valdivieso Cacique et al. | |
| 8,971,597 B2 | 3/2015 | Zhao et al. | |
| 9,005,112 B2 | 4/2015 | Hasser et al. | |
| 9,044,257 B2 | 6/2015 | Fielding et al. | |
| 9,107,683 B2 | 8/2015 | Hourtash et al. | |
| 9,108,318 B2 | 8/2015 | Diolaiti | |
| 9,259,282 B2 | 2/2016 | Azizian et al. | |
| 9,295,524 B2 | 3/2016 | Schena et al. | |
| 9,296,104 B2 | 3/2016 | Swarup et al. | |
| 9,298,194 B2 | 3/2016 | Lee et al. | |
| 9,339,344 B2 | 5/2016 | Schena et al. | |
| 9,345,387 B2 | 5/2016 | Larkin | |
| 9,345,544 B2 | 5/2016 | Hourtash et al. | |
| 9,358,682 B2 | 6/2016 | Ruiz Morales | |
| 9,375,284 B2 | 6/2016 | Hourtash | |
| 9,415,510 B2 | 8/2016 | Hourtash et al. | |
| 9,468,501 B2 | 10/2016 | Hourtash et al. | |
| 10,717,194 B2 | 7/2020 | Griffiths et al. | |
| 2006/0178556 A1 | 8/2006 | Hasser et al. | |
| 2006/0261770 A1 | 11/2006 | Kishi et al. | |
| 2009/0326322 A1 | 12/2009 | Diolaiti et al. | |
| 2010/0137882 A1 | 6/2010 | Quaid, III et al. | |
| 2011/0301757 A1 | 12/2011 | Jones et al. | |
| 2013/0325029 A1 | 12/2013 | Hourtash et al. | |
| 2014/0051049 A1 | 2/2014 | Jarc et al. | |
| 2014/0130810 A1 | 5/2014 | Azizian et al. | |
| 2014/0135985 A1 | 5/2014 | Coste-Maniere et al. | |
| 2014/0142593 A1* | 5/2014 | Fielding ................ | A61B 34/30 606/130 |
| 2014/0316430 A1 | 10/2014 | Hourtash et al. | |
| 2015/0032126 A1 | 1/2015 | Nowlin et al. | |
| 2015/0313452 A1 | 11/2015 | Hasser et al. | |
| 2016/0038011 A1 | 2/2016 | Diolaiti et al. | |
| 2016/0184032 A1 | 6/2016 | Romo et al. | |
| 2016/0242858 A1* | 8/2016 | Moctezuma de la Barrera ......... A61B 34/20 |
| 2016/0345929 A1 | 12/2016 | Azizian et al. | |
| 2018/0042543 A1* | 2/2018 | Jenkins ................ | G16H 20/30 |
| 2019/0054620 A1 | 2/2019 | Griffiths et al. | |

FOREIGN PATENT DOCUMENTS

| | | |
|---|---|---|
| WO | WO-2013181516 A1 | 12/2013 |
| WO | WO-2014151550 A2 | 9/2014 |
| WO | WO-2015120008 A1 | 8/2015 |
| WO | WO-2015142796 A1 | 9/2015 |
| WO | WO-2015142930 A1 | 9/2015 |
| WO | WO-2015142953 A1 | 9/2015 |

OTHER PUBLICATIONS

International Search Report and Written Opinion for Application No. PCT/US2017/016427, dated May 12, 2017, 10 pages.
Vertut, Jean and Philiipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM AND METHOD FOR COLLISION AVOIDANCE USING VIRTUAL BOUNDARIES

RELATED APPLICATIONS

This application is a continuation of co-pending U.S. patent application Ser. No. 16/079,970, filed Aug. 24, 2018, which is a U.S. National Stage patent application of International Patent Application No. PCT/US2017/016427 filed on Feb. 3, 2017, the benefit of which is claimed, and claims priority to and the benefit of the U.S. Provisional Patent Application 62/300,706, entitled "SYSTEM AND METHOD FOR COLLISION AVOIDANCE USING VIRTUAL BOUNDARIES" filed Feb. 26, 2016, each of which is incorporated by reference herein in its entirety.

TECHNICAL FIELD

The present disclosure relates generally to teleoperation of devices with repositionable arms and more particularly to collision avoidance using virtual boundaries.

BACKGROUND

More and more instruments are being replaced with autonomous and semiautonomous devices. This is especially true in the hospitals of today with large arrays of autonomous and semiautonomous medical devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These medical devices provide both advantages and challenges to the personnel operating them. Many of these medical devices may be capable of autonomous or semi-autonomous motion of one or more repositionable arms and/or end effectors. It is also common to operate the medical devices via teleoperation using one or more input controls on an operator workstation to control the motion and/or operation of the repositionable arms and/or the end effectors. Examples of such devices include the da Vinci® Surgical System commercialized by Intuitive Surgical, Inc. of Sunnyvale, Calif. When the medical device is operated remotely from the operator workstation and/or the end effectors are being used in an area not directly visible to the operator, such as during computer-assisted surgery when the end effectors are hidden by patient anatomy, surgical drapes, and/or the like, it may complicate the operator's ability to detect and/or avoid collisions between the one or more repositionable arms that could result in damage to the medical device, injury to a patient or other personnel, and/or failures in a sterile field.

Collision avoidance between repositionable devices, such as the repositionable arms of a medical device, is typically addressed in a motion planning context. In this context, the motion plans for each of the repositionable arms are determined, and the future motions of the repositionable arms are evaluated to determine whether collisions between the repositionable arms will occur, with appropriate corrections to the motion plans occurring to avoid the collision. This approach is often far from ideal for repositionable arms controlled via teleoperation because control of the repositionable arms is directed in real-time by an operator (i.e., the operator is unable to perceive a delay between making an input and the resulting movement) so that motion plans for the repositionable arms are not known and cannot serve as the basis for collision avoidance determinations. As an alternative to collision avoidance, a collision detection approach may be used that provides feedback to the operator when a collision occurs between the repositionable arms. But, a collision detection approach suffers disadvantages. Actual collisions often result in a poor user experience for the operator. And, at a minimum, collision detection between arms often detects the collision too late to avoid damage to the sterile field, because the sterile drapes covering the arms typically contact each other before the repositionable arms collide, and a drape trapped between two colliding arms may be torn. Some hybrid collision avoidance-collision detection systems operate by modeling large volumes, typically with planar surfaces and which are often convex in shape, that circumscribe the links and joints of the repositionable arms. In some cases, the links and joints of the repositionable arm are divided into segments with each segment having its own three-dimensional circumscribing primitive, such as a sphere, cylinder, or box, with an overall circumscribing volume being constructed by taking a union of the circumscribing primitives. As the repositionable arms are operated, collision detection is applied to the circumscribing volumes so that "collisions" between the circumscribing volumes are detected and reacted to prior to an actual collision occurring. Other approaches include providing separate non-intersecting workspaces for each of the repositionable arms that eliminate the need for additional collision detection or avoidance. These hybrid approaches, however, are often too conservative in predicting collisions as the circumscribing volumes are often overly large for the circumscribed links and joints and these overly large circumscribing volumes as well as the separate workspaces often interfere with the ability to operate the repositionable arms with separation distances smaller than the circumscribing volumes.

Accordingly, improved methods and systems for avoid collisions between the repositionable arms of computer-assisted medical devices are desirable.

SUMMARY

Advantageously, systems and methods in accordance with the present invention allow the teleoperation of devices with repositionable arms with superior collision avoidance behavior over motion-planning based collision avoidance or collision detection approaches. In one aspect, high fidelity CAD (computer-aided drafting or computer-aided modeling) or kinematic models of the repositionable models are used to create a virtual model of each of the repositionable arms. The virtual models are then expanded by a predetermined distance to create a virtual boundary defining a corresponding virtual buffer zone around each of the joints and links in the repositionable arms. As the repositionable arms are controlled via teleoperation, a collision engine determines when there is an overlap between the virtual boundaries indicating that at least two of the repositionable arms have moved to within a near proximity to each other. A physical model of surface or volume interaction, such as an elastic model based on surface or volume penetration, is then applied by a physics engine to determine a feedback force that is applied to the repositionable arms that pushes the repositionable arms apart so as to reduce or eliminate the overlap in the virtual boundaries. The feedback force is then mapped to changes in the forces or torques applied to those joints of the repositionable arms that allow the repositionable arms are pushed away from a potential collision before an actual collision occurs. In some optional aspects, the feedback force is also mapped to haptic feedback that is applied to the input controls used by the operator to teleoperate the repositionable arms so as to oppose the operator's ability to command the repositionable arms toward a collision condition. In this way, the operator "feels" a collision in one or more of the input controls before it occurs, and in response the operator can move the repositionable arms away from the potential collision.

In some aspects, the use of the virtual models and the virtual boundary to generate the feedback force provides advantages over more traditional collision detection approaches. For example, relying on actual collisions between the repositionable arms, such as those detected by noticing differences between the desired positions and the actual positions of the repositionable arms, often generates poor operator force feedback results that have poor collision directionality and lower magnitudes, which generally do not provide for good haptic feedback on the one or more input controls. For example, it is well known that when physical contact between repositionable arms is used to reflect haptic feedback in the input controls used to control those repositionable arms that there is an attendant compromise between the fidelity and forcefulness of the haptic feedback and stability in the control of the repositionable arms. Thus, simply increasing an amplitude in the force fed back haptically to the input controls is likely to result in unacceptable loss of stability in the control of the repositionable arms. In contrast, because in inventive aspects the feedback force is derived from an overlap in the virtual boundaries and not an actual collision, the full feedback control path through the repositionable arms is bypassed so that control stability may be maintained even though stronger haptic feedback is applied. In addition, stronger collision directionality can be determined and higher haptic feedback magnitudes can be obtained via appropriate scaling. This enhanced force and haptic feedback provides additional enhancements to the operator experience so that the shape and contours of one repositionable arm may optionally be felt in the input controls of another repositionable arm, and it optionally allows teleoperation where the repositionable arms move as if to "slide" along each other. (The motion is analogous to honing a knife edge by moving the knife and a steel across one another, but the arms do not touch and instead maintain a defined separation distance.) In addition, the virtual boundaries allow the repositionable arms to operate in close proximity to each other, while also avoiding actual collisions that could damage the repositionable arms or the sterile drapes used to create the sterile field around the repositionable arms.

In some aspects, the predetermined distances used to create the virtual boundaries are controlled to allow close operation of the repositionable arms while avoiding collisions without overly limiting the range of motions through which the repositionable arms may be operated. In some examples, the predetermined distance is adjusted based on the modeling and kinematic calibration of the repositionable arms, with a smaller predetermined distance being used for repositionable arms that are controllable with higher accuracy. In some cases the predetermined distance is set to approximately the same value as the kinematic calibration for the respective links and joints of the repositionable arms. In some cases a smaller predetermined distance is used for links and joints located more proximally to a mechanical base on the repositionable arms, and a higher predetermined distance is used for links and joints located more distally on the repositionable arms. In some cases, the predetermined distance may optionally be reduced to zero or even set to a negative value where collisions are allowed, such as near the distal tips of end effectors and/or instruments mounted to the distal ends of the repositionable arms. In some cases, collision avoidance may optionally be disabled for portions of the repositionable arms where collisions are allowed.

Consistent with some embodiments, a computer-assisted medical device includes a first repositionable arm, a second repositionable arm, a first input control, and a control unit including one or more processors. The first repositionable arm include a plurality of first joints, a plurality of first links, and a first distal end configured to support a first instrument. The second repositionable arm includes a plurality of second joints, a plurality of second links, and a second distal end configured to support a second instrument. The first input control is configured to provide movement commands for the first instrument. The control unit is coupled to the first repositionable arm, the second repositionable arm, and the first input control. The control unit determines first positions of the plurality of first joints and second positions of the plurality of second joints, uses a first virtual model of the first repositionable arm and the first positions to determine a plurality of first virtual boundaries around the first repositionable arm, uses a second virtual model of the second repositionable arm and the second positions to determine a plurality of second virtual boundaries around the second repositionable arm, determines a first overlap between a first one of the plurality of first virtual boundaries and a first one of the plurality of second virtual boundaries, determines a first overlap force on the first repositionable arm due to the first overlap, maps the first overlap force to first virtual torques on multiple first joints proximal to the first overlap, determines a first tip force on a distal end of the first instrument based on the first virtual torques, and applies the first tip force as a first feedback force on the first instrument and the first repositionable arm.

Consistent with some embodiments, a method of collision avoidance performed by a control unit includes determining positions of a plurality of first joints of a first repositionable arm and determining second positions of a plurality of second joints of a second repositionable arm. A first instrument is mounted to a distal end of the first repositionable arm. A first instrument is mounted to a distal end of the second repositionable arm. The method further includes determining positions of a plurality of first virtual boundaries around the first repositionable arm using the first positions and a first virtual model of the first repositionable arm, determining positions of a plurality of second virtual boundaries around the second repositionable arm using the second positions and a second virtual model of the second repositionable arm, determining a first overlap between a first one of the first virtual boundaries and a first one of the second virtual boundaries, determining a first overlap force on the first and second repositionable arms due to the first overlap, mapping the first overlap force to first virtual torques on first joints of the plurality of first joints proximal to a first overlap position of the first overlap, determining a first tip force on a distal end of the first instrument based on the first virtual torques, applying the first tip force as a first feedback force on the first instrument and the first repositionable arm, and applying the first tip force as a first haptic feedback force to a first input control configured to provide movement commands for the first instrument.

Consistent with some embodiments, a computer-assisted manipulation device comprises a repositionable arm, an input control, and a control unit comprising one or more processors. The repositionable arm has a plurality of joints, a plurality of links, and a distal end configured to support an instrument. The input control is configured to provide movement commands for the instrument. The control unit is coupled to the repositionable arm and the input control, wherein the control unit is configured to: determine joint positions of the plurality of joints; use a virtual model of the repositionable arm and the joint positions to determine a plurality of virtual boundaries, the plurality of virtual boundaries around the repositionable arm or the instrument; determine an object virtual boundaries around an object; determine an overlap between the object virtual boundary and a virtual boundary of the plurality of virtual boundaries; determine an overlap force on the repositionable arm due to the overlap; map the overlap force to a virtual torque on a joint of the plurality of joints; determine a tip force on a distal end of the instrument using the virtual torque; and apply the tip force as a feedback force on the instrument and the repositionable arm.

Consistent with some embodiments, a non-transitory machine-readable medium stores machine-readable instructions which when executed by one or more processors associated with a computer-assisted medical device are adapted to cause the one or more processors to perform a method. The method includes determining positions of a plurality of first joints of a first repositionable arm and determining second positions of a plurality of second joints of a second repositionable arm. A first instrument is mounted to a distal end of the first repositionable arm. A second instrument is mounted to a distal end of the second repositionable arm. The method further includes determining positions of a plurality of first virtual boundaries around the first repositionable arm using the first positions and a first virtual model of the first repositionable arm, determining positions of a plurality of second virtual boundaries around the second repositionable arm using the second positions and a second virtual model of the second repositionable arm, determining a first overlap between a first one of the first virtual boundaries and a first one of the second virtual boundaries, determining a first overlap force on the first and second repositionable arms due to the first overlap, mapping the first overlap force to first virtual torques on the first joints proximal to a first position of the first overlap, determining a first tip force on a distal end of the first instrument based on the first virtual torques, applying the first tip force as a first feedback force on the first instrument and the first repositionable arm, and applying the first tip force as a first haptic feedback force to a first input control configured to provide movement commands for the first instrument.

BRIEF DESCRIPTION OF THE DRAWINGS

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
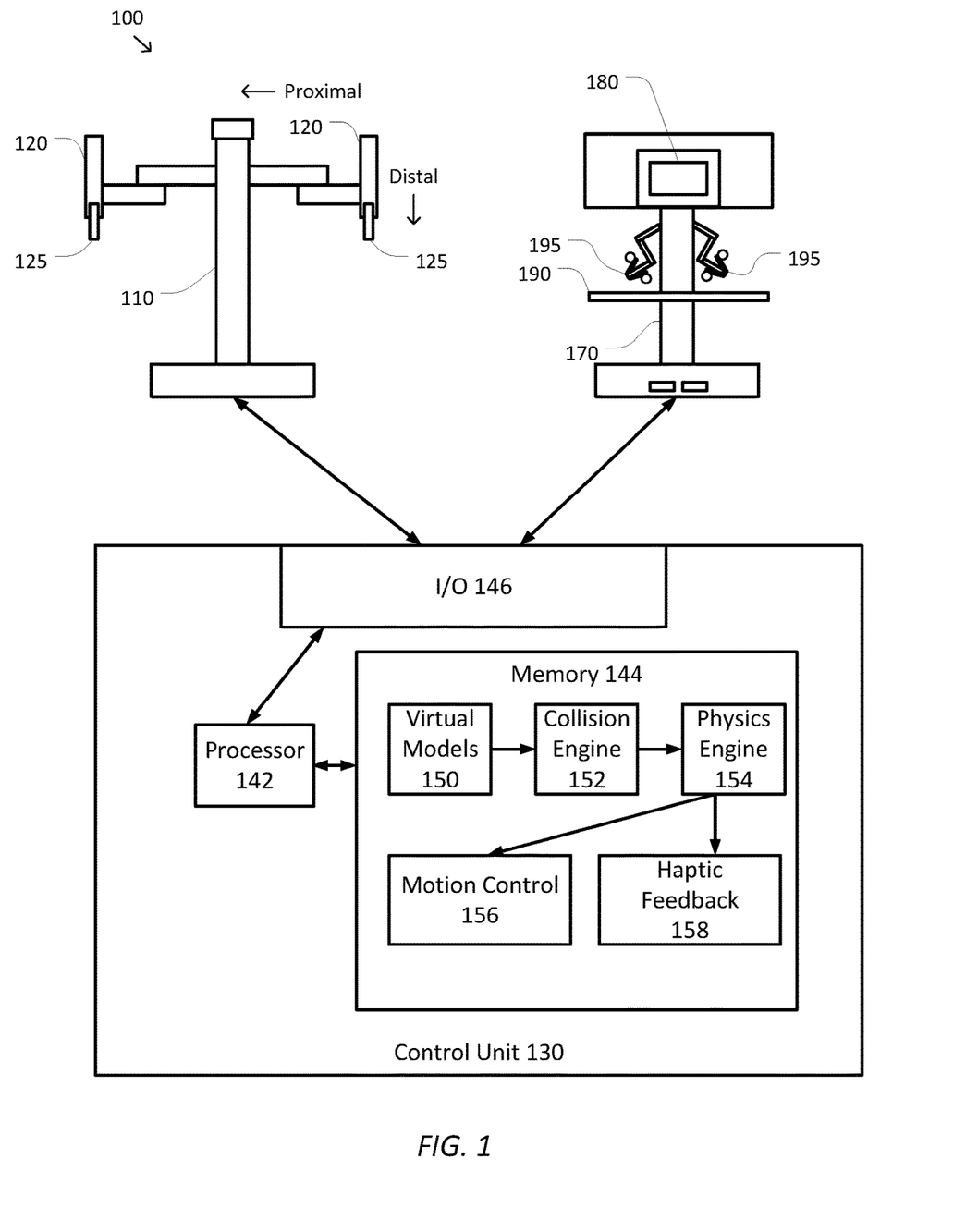
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more repositionable arms 120. In some examples, each of the one or more repositionable arms 120 may optionally include one or more links and one or more joints with the one or more joints allowing articulation of the one or more links. In some examples, each of the one or more repositionable arms 120 may optionally include one or more flexible members, such as a steerable tube. Each of the one or more repositionable arms 120 is configured to support one or more end effectors 125 that may optionally be mounted to a distal end of a respective one of the repositionable arms 120. An assembly of a repositionable arm 120 with a mounted end effector 125 can be termed an "arm-and-end-effector assembly." In some examples, device 110 may be consistent with a computer-assisted manipulation device, such as a computer-assisted medical device. A specific example of a computer-assisted medical device is a teleoperated surgical device. The one or more end effectors 125 include surgical instruments, imaging devices, and/or the like. In some examples, the surgical instruments include clamps, grippers, retractors, cautery tools, suction tools, suturing devices, and/or the like. In some examples, the imaging devices include stereo- and mono-scopic imaging devices, imaging devices in the visible and infrared ranges, steerable endoscopic imaging devices, and/or the like. In some examples, each of the repositionable arms 120 and/or end effectors 125 may optionally be configured with a remote center of motion during operation. The remote center of motion is a location that maintains a stationary position in space even though links and/or joints of a corresponding repositionable arm 120, end effector 125, or both change in orientation or angular or linear position. For example, the remote center of motion may remain in a stationary position even where an orientation of the end effector 125 relative to the remote center of motion has changed. In some examples, the remote center of motion may optionally correspond to a portion of the corresponding repositionable arm 120 and/or end effector 125 that is inserted through a body wall of a patient during operation. In some examples, the remote center of motion is allowed to move within a range about a fixed location in space. As a specific example, where the remote center of motion is for a portion inserted through the body wall of patient, the range may be defined using criteria such as the flexibility and material characteristics of the body wall, the amount of motion that can be accommodated while not causing excess trauma to the patient, and the like.

Device 110 is coupled to a control unit 130 via an input/output (I/O) interface 146. I/O interface 146 may optionally include one or more cables, connectors, ports, and/or buses, and it may optionally further include one or more networks with one or more network switching and/or routing devices. Control unit 130 includes a processor 142 coupled to memory 144 and to I/O interface 146. Operation of control unit 130 is controlled by processor 142. And although control unit 130 is shown with only one processor 142, it is understood that processor 142 is representative of one or more central processing units, multi-core processors, microprocessors, microcontrollers, digital signal processors, field programmable gate arrays (FPGAs), application specific integrated circuits (ASICs), and/or the like in control unit 130. Control unit 130 may optionally be implemented as a stand-alone subsystem and/or board added to a computing device or as a virtual machine.

Memory 144 is used to store software executed by control unit 130 and/or one or more data structures used during operation of control unit 130. Memory 144 includes one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Control unit 130 is further coupled to an operator workstation 170 via I/O interface 146. Operator workstation 170 is used by an operator, such as a surgeon, to control the movement and/or operation of the repositionable arms 120 and/or the end effectors 125 using teleoperation. To support teleoperation of the repositionable arms 120, operator workstation 170 includes a display system 180 for displaying images of at least portions of one or more of the repositionable arms 120 and/or end effectors 125. For example, display system 180 can be used when it is impractical and/or impossible for the operator to see the repositionable arms 120 and/or the end effectors 125 as they are being used. Operator workstation 170 further includes a console workspace with one or more input controls 195 (also called "master controls 195") that are usable for device 110, the repositionable arms 120, and/or the end effectors 125. Each of the input controls 195 is coupled to the distal end of their own repositionable arms so that movements of the input controls 195 are detected by the operator workstation 170 and communicated to control unit 130 through I/O interface 146. To provide improved ergonomics, the console workspace may optionally include one or more rests, such as an arm rest 190 on which operators may rest their arms while manipulating input controls 195. In some embodiments, device 110, operator workstation 170, and control unit 130 may optionally correspond to a da Vinci® Surgical System commercialized by Intuitive Surgical, Inc. of Sunnyvale, Calif. It will be understood that control unit 130 may optionally be separate from device 110 and workstation 170, be incorporated into either device 110 or workstation 170, or be distributed between device 110 and workstation 170.

Referring back to control unit 130, memory 144 includes several modules, applications, data structures, and/or the like that include virtual models 150, a collision engine 152, a physics engine 154, a motion control module 156, and a haptic feedback module 158. The virtual models 150, collision engine 152, physics engine 154, and/or motion control module 156 are used to support autonomous and/or semi-autonomous control of device 110, and each may optionally include one or more application programming interfaces (APIs) for receiving inputs, sensor data, instructions, and/or the like for supporting the control of device 110, including repositionable arms 120 and end effectors 125. And although virtual models 150, collision engine 152, physics engine 154, motion control module 156, and haptic feedback module 158 are depicted as software applications, each of the virtual models 150, collision engine 152, physics engine 154, motion control module 156, and haptic feedback module 158 may optionally be implemented using hardware, software, and/or a combination of hardware and software.

When input controls 195 are used to control end effectors 125 using teleoperation, sensors coupled to the repositionable arms of operator workstation 170 are used to sense the positions, velocities, and/or orientations of input controls 195. The sensed positions, velocities, and/or orientations are then passed to control unit 130 through I/O interface 146, where they are processed by motion control module 156 to compute suitable forces and/or torques for the joints of repositionable arms 120 and end effectors 125 that will teleoperate end effectors 125 to corresponding positions and/or orientations that track input controls 195. The computed forces and/or torques are then provided to respective joints in the repositionable arms 120 and end effectors 125 using I/O interface 146. Examples of teleoperated systems consistent with this approach are further described in U.S. Pat. No. 6,424,885, entitled "Camera Referenced Control in a Minimally Invasive Surgical Apparatus," which is hereby incorporated by reference in its entirety.

Control unit 130 additionally supports collision avoidance between repositionable arms 120 and/or end effectors 125 using virtual boundaries. More specifically, virtual models 150 include high fidelity CAD and/or kinematic models of the links and joints of repositionable arms 120 and/or end effectors 125 that are used to model at least the positions of the exterior surfaces of the joints and links that make up repositionable arms 120 and/or end effectors 125. Virtual models 150 are further parameterized so that as outputs from sensors associated with the joints are input to control unit 130 using I/O interface 146, position and orientation data about the joints may be used by virtual models 150 to generate current positions of the exterior surfaces of the joints and links. The accuracy attainable using virtual models 150 may optionally depend on several practical limitations in determining the positions of repositionable arms that impact the ability to generate good kinematic calibration for the repositionable arms 120. For example, the accuracy of virtual models 150 is typically affected by a combination of manufacturing tolerances, calibration accuracy, sensor accuracy, backlash, wear and dynamics of each of the repositionable arms 120, and/or the like. In addition, in a repositionable arm 120, which includes a series of links, where each link defines a geometric transform from a proximally coupled link to a distally coupled link where the most proximal link may optionally be shared by multiple repositionable arms and defines an origin of each of the geometric transforms. The geometric transform defined by each link has intrinsic errors due to variability in the mechanical assembly and manufacturing of the link and some or all of the transform may be measured for each link built to achieve high kinematic accuracy. In addition, where links meet at repositionable elements, such as joints, there is a variable geometric transformation between one link and the next and sensors are typically installed and calibrated to provide a true angle or displacement and axis of articulation. In addition, the transform defined by each link may vary as loads are applied to the link, due for example to flexibility in the link, and may optionally be accounted for using a dynamic model of the link. Some factors such as backlash in the sensors and/or loose attachments between links are often challenging to estimate and degrade kinematic accuracy. Additionally, the accuracy of the models typically degrades for links located more distally on the repositionable arm. In some embodiments, limitations in the kinematic calibration may optionally allow virtual models 150 to position external surfaces of within 6-12 mm of their actual position. Additionally, modeling accuracy to within 6-12 mm also provides reasonable clinical outcomes when additional positional and/or imaging feedback are used to monitor the positions and orientations of repositionable arms 120. In some examples, surface details or features of repositionable arms 120 and/or end effectors 125 that are smaller than the modeling accuracy are optionally simplified so that exterior surfaces of the links and/or joints are modeled using simpler, fewer, and/or predominantly convex surface models.

In some embodiments, one or more registration markers, fiducial markers, and/or the like mounted on repositionable arms 120 and/or end effectors 125 may alternatively be tracked using one or more tracking sensors, such as an imaging device, to supplement and/or replace the sensor inputs to determine the orientations of one or more of the joints in repositionable arms 120 and/or end effectors 125. Optionally, other position and shape sensing components are additionally and/or alternatively used, such as optical fiber shape sensors using Fiber Bragg Grating technology, such as the optical fiber shape sensors disclosed in U.S. Pat. No. 7,720,322 entitled "Fiber Optic Shape Sensor," which is hereby incorporated by reference in its entirety.

Virtual models 150 further include virtual boundaries that are extended beyond the exterior surfaces by corresponding predetermined distances so as to create virtual boundaries with virtual buffer zones around the joints and links of repositionable arms 120 and/or end effectors 125. In some examples, lengths to which the virtual boundaries are extended beyond the exterior surfaces are selected so that any positional inaccuracies in the actual positions of the exterior surfaces of joints and links (e.g., due to errors from the modeling and/or kinematic calibration limitations as discussed above) help ensure that the actual positions of the exterior surfaces are within the virtual boundaries. In some examples, the predetermined distances may be selected to be approximately the same or slightly larger than the corresponding modeling and/or kinematic calibration for the corresponding joints or links. In some examples, the predetermined distance may optionally be larger for joints and/or links located toward the distal ends of repositionable arms 120 and/or end effectors 125 to reflect the generally less accurate modeling and/or kinematic calibration of the more distal joints and/or links. And, the predetermined distance may be selected in whole or in part to allow sufficient space for sterile drapes that cover the repositionable arms 120 to avoid damaging contact that might result in tearing or puncturing a drape. In some examples, the lengths to which the virtual boundaries are extended may optionally be between 6-12 mm.

As repositionable arms 120 and end effectors 125 are manipulated and/or teleoperated using input controls 195, virtual models 150 are used to determine current positions of the virtual boundaries. The current positions of the virtual boundaries are then passed to collision engine 152 to determine whether there is a virtual collision between virtual boundaries of different repositionable arms 120 and/or end effectors 125. In some examples, the virtual collision is detected whenever there is an intersection or overlap between virtual boundaries of different repositionable arms 120 and/or end effectors 125 or alternatively due to more than one overlap in the corresponding virtual buffer zones. Each of the overlaps in virtual boundaries identifies a virtual collision between the corresponding repositionable arms 120 and/or end effectors 125.

Each of the overlaps is then passed to physics engine 154 to determine a corresponding a virtual overlap force of the corresponding virtual collision. In some examples, physics engine 154 determines a magnitude of the corresponding virtual overlap force based on one or more of an amount of overlap, a depth of the overlap, a volume of the overlap, an area of contact of the overlap, and/or the like. In some examples, physics engine 154 determines a direction of the corresponding virtual overlap force based on a direction of a maximum overlap between the respective virtual boundaries and/or based on a surface normal of the respective virtual boundaries at the overlap. In some examples, physics engine 154 uses a virtual spring model with a linear or alternatively a non-linear constant to determine the magnitude of the virtual overlap force. In some examples, physics engine 154 uses a deformable material model, such a gas or fluid dynamics model, for the regions within the virtual boundaries so that the volume of the overlap in combination with a coefficient of resiliency for virtual material in the regions within the virtual boundaries provides a displacing force from which the virtual overlap force is derived. Examples of models generating virtual feedback forces are described in further detail in International Patent Publication No. WO 2015/120008 entitled "System and Method for Dynamic Virtual Collision Objects," which is hereby incorporated by reference in its entirety. In some embodiments, physics engine 154 may optionally further include surface interaction effects between the overlapping virtual boundaries based on one or more of the deformable material model, damping, sliding friction, surface roughness, and/or the like. In some examples, the surface interaction effects may optionally result in feedback forces perpendicular to the virtual overlap force that model resistance to sliding one virtual boundary along another virtual boundary.

The virtual overlap force is then used to determine a corresponding feedback on one or all of the respective repositionable arms, end effectors, or arm-and-end-effector assemblies associated with the virtual collision. Without loss of generality, this process is described below for one of the respective repositionable arms, end effectors, or arm-and-end effector assemblies, which is generically referred to as the respective repositionable arm and/or end effector. It is understood that different repositionable arms and/or end effectors have different kinematics and thus would be analyzed using their own respective versions of the various functions and mappings. In some examples, a respective Jacobian inverse or Jacobian pseudo-inverse for the respective repositionable arm and/or end effector between the point of overlap and the joints of the respective repositionable arm and/or end effector located proximal to the point of overlap is used in this determination. In some examples, a Jacobian pseudo-inverse may be calculated using a Jacobian transpose. The Jacobian inverse or Jacobian pseudo-inverse is used to map the virtual overlap force to virtual joint torques in each of the joints that is located proximal to the point of overlap in the respective repositionable arm and/or end effector. In these examples, computation of the virtual joint torques is limited to those joints proximal to the point of overlap. In many cases, the overlap can be satisfactorily reduced and/or eliminated using only joints proximal to the point of the virtual collision. In other examples, computation of the virtual joint torques are not thus limited, and are also determined for those joints not proximal to the point of overlap.

In some examples, the virtual joint torques are then used to determine corresponding tip forces for the respective repositionable arm and/or end effector. A function relating the joint torques and tip forces may be used. In some examples, an inverse of the Jacobian inverse or Jacobian pseudo inverse (e.g., an inverse of the Jacobian transpose) between the tip of the respective end effector and the joints in the respective repositionable arm and/or end effector can then be used with the virtual torques in the joints, to determine a corresponding tip force that could be applied to a distal-most tip of the respective repositionable arm and/or end effector to emulate the effects of the virtual collision. In some examples, the corresponding tip force is then provided to motion control module 156 to be applied as a feedback to the motion control of the respective repositionable arm and/or end effector so that the respective repositionable arm and/or end effector opposes the virtual collision and resists being teleoperated closer to an actual collision. In some examples, the feedback of the corresponding tip force is superimposed on the motion dictated by the teleoperated commands for the respective repositionable arm and/or end effector.

In some embodiments, when more than one overlap is detected by collision engine 152, a respective virtual overlap force for each respective overlap is separately determined. The respective virtual overlap force is then used to generate respective virtual torques for both the repositionable arms and/or end effectors associated with each respective overlap. In some examples, the respective virtual torques may be superimposed for their corresponding repositionable arms and/or end effectors to determine an overall corresponding tip force for the corresponding repositionable arm and/or end effector that is provided to motion control module 156. Alternatively, the overall corresponding tip force is determined by superimposing separate tip forces generated for each of the overlaps.

In some embodiments, the tip force for each of the repositionable arms and/or end effectors subject to a virtual collision is then provided to haptic feedback module 158 to provide haptic feedback to the operator through respective input controls 195. In some examples, the tip force is scaled to reflect differences in relative force used to manipulate the repositionable arm 120 and/or end effector 125 and the force used to manipulate the corresponding input control 195. In some examples, an inverse of a Jacobian transpose for the respective input control 195 is used to map the tip force to respective joint torques in the repositionable arm of the input control 195 to apply haptic feedback to the operator. Alternatively, in some embodiments, differences between actual positions of the repositionable arms and/or end effectors and corresponding commanded positions of the repositionable arms and/or end effectors are used to determine the haptic feedback on each of the respective input controls 195.

Modeling the overlap forces using the virtual boundaries provides for one or more advantages to collision avoidance. First, because a virtual overlap force is not determined until after an overlap in virtual boundaries is detected, embodiments may be configured such that the effects of virtual collisions are only determined when corresponding repositionable arms and/or end effectors are in close proximity to each other and ignored at other times. Second, use of the virtual overlap enables accurate models of both (a) a severity of the virtual collision and (b) corresponding surface normals for the virtual collision. These more accurate models enable determination of more accurate directions and magnitudes of feedback forces in the respective repositionable arms and/or end effectors for pushing the respective repositionable arms and/or end effectors away from the virtual collision. This helps to prevent actual collisions between the respective repositionable arms and/or end effectors.

According to some embodiments, various optional repositionable arm and/or end effector motions may be used to resolve a virtual collision in which one or more overlaps exist. One repositionable arm and/or end effector may stay stationary while the second repositionable arm and/or end effector moves in any combination of one, two, or three Cartesian translations and orientations (the various combinations are not listed here to avoid excessive description) to increase a respective distance between each of the overlaps in the direction of the respective surface normal. Alternatively, both of the repositionable arms and/or end effectors may move in any combination of one, two, or three Cartesian translations and orientations to increase the respective distance between each of the overlaps in the direction of the respective surface normal. In some examples, the relative motion between the two repositionable arms and/or end effectors may optionally result is a sliding-type motion that resembles a first link sliding across a second, stationary link, or that resembles two links sliding across one another. In some examples, the sliding motion may optionally include a rolling motion, so that the resulting motion resembles a first link rolling around a second, stationary link, or two links rolling around each other. In various embodiments, the links can be modeled as sticks.

Thus, for a link of an articulated arm and/or end effector with a longitudinal axis defined between the opposite ends of the link, the location of the overlap between the two respective virtual boundaries may move along the link in a direction generally aligned with the longitudinal axis, and/or the location of the overlap between the two respective virtual boundaries may generally move along a curve on the surface of the link. Similarly, the location of the overlap between the two respective virtual boundaries may move along the surface of either or both of the respective virtual boundaries boundary in a direction generally aligned with the longitudinal axis, or the location of the overlap between the two respective virtual boundaries may move along a curve on the surface of one or both of the respective virtual boundaries. As a result, the two repositionable arms and/or end effectors appear to slide with reference to each other, but with a distance between them to prevent damage to the repositionable arms and/or end effectors and/or to sterile drapes covering the repositionable arms and/or end effectors. In some examples, the operator may optionally experience this sliding motion in one or both of the input controls, or the sliding motion may optionally occur without the operator experiencing any sensation in the input controls. In some embodiments, additional surface interaction effects may optionally be included in the feedback that results from the overlap of the virtual boundaries. In some examples, the feedback may optionally include forces perpendicular to the virtual overlap force that model resistance to the sliding motion. In some examples, the amount of resistance to the sliding motion may be proportional to the virtual overlap force consistent with modeling of friction between two surfaces being slid against each other.

In some embodiments, other configurations and/or architectures may be used with computer-assisted system 100. In some examples, control unit 130 may optionally be included as part of operator workstation 170 and/or device 110. In some embodiments, computer-assisted system 100 is usable in an operating room and/or an interventional suite. And although computer-assisted system 100 is shown as including only one device 110 with two repositionable arms 120, one of ordinary skill would understand that computer-assisted system 100 may optionally include any number of devices with repositionable arms and/or end effectors of similar and/or different design from device 110. In some examples, each of the devices may include one or three or more repositionable arms 120 and/or end effectors 125.

Figure 2A:
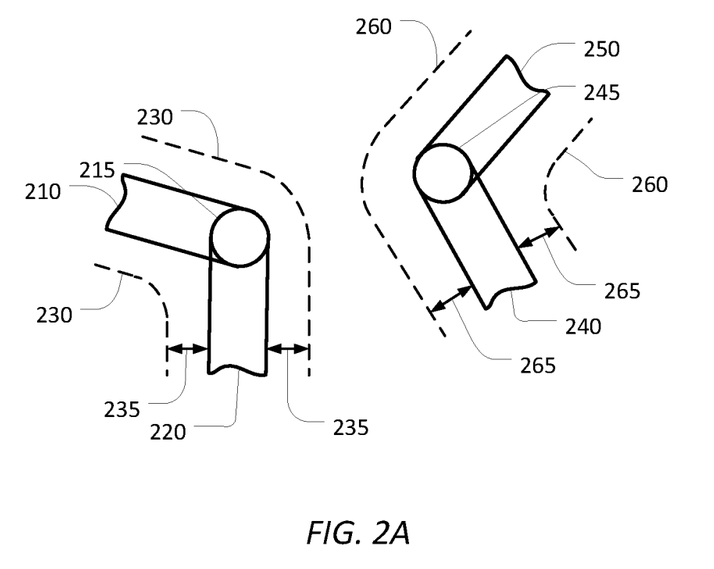
FIGS. 2A and 2B are simplified diagrams of portions of two repositionable arms with virtual boundaries according to some embodiments.
Figure 2B:
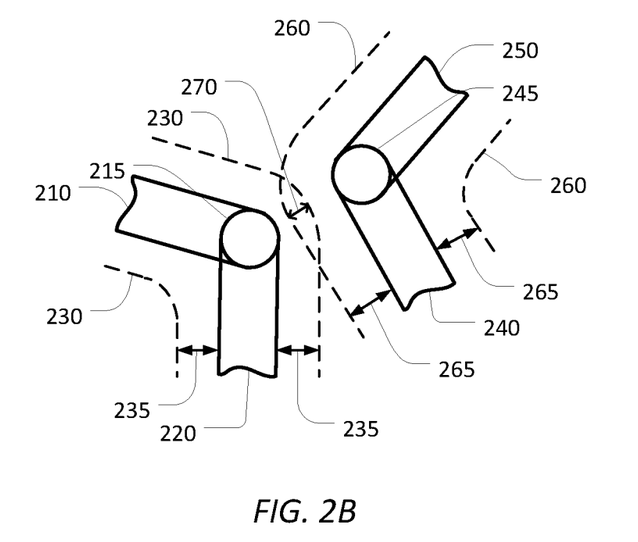

FIGS. 2A and 2B are simplified diagrams of portions of two repositionable arms with virtual boundaries according to some embodiments. FIG. 2A shows the two repositionable arms without an overlap between their respective virtual boundaries and FIG. 2B shows the same repositionable arms with an overlap between their respective virtual boundaries. In some examples, the two repositionable arms are consistent with the repositionable arms 120 and/or end effectors 125 of device 110.

In more detail, FIG. 2A shows a portion of a first repositionable arm having links 210 and 220 coupled by a joint 215. The first repositionable arm also has a virtual boundary 230 that is extended beyond the exterior surfaces of links 210 and 220 and joint 215 by a predetermined distance 235. And although the first repositionable arm is shown in FIG. 2A in two dimensions, it is understood that links 210 and 220 as well as joint 215 extend into three dimensions and that virtual boundary 230 extends around links 210 and 220 and joint 215 in all three dimensions. As joint 215 is manipulated (e.g., to change an angle between links 210 and 220) a corresponding shape of virtual boundary 230 is changed accordingly. In some examples, virtual boundary 230 and predetermined distance 235 are consistent with a virtual model of the first repositionable arm included in virtual models 150.

FIG. 2A also shows a portion of a second repositionable arm having links 240 and 250 coupled by a joint 245. The second repositionable arm also has a virtual boundary 260 that is extended beyond the exterior surfaces of links 240 and 250 and joint 245 by a predetermined distance 265. And although the second repositionable arm is shown in FIG. 2A in two dimensions, it is understood that links 240 and 250 as well as joint 245 extend into three dimensions and that virtual boundary 260 extends around links 240 and 250 and joint 245 in all three dimensions. As joint 245 is manipulated (e.g., to change an angle between links 240 and 250) a corresponding shape of virtual boundary 260 is changed accordingly. In some examples, virtual boundary 260 and predetermined distance 265 are consistent with a virtual model of the second repositionable arm included in virtual models 150.

When the first and second repositionable arms of FIG. 2A are moved closer to each other, an overlap between virtual boundary 230 and virtual boundary 260 may occur, such as is depicted in FIG. 2B at overlap 270. When overlap 270 is detected by collision engine 152, several characteristics of overlap 270 are determined. For example, even though virtual boundary 230 and virtual boundary 260 overlap by varying amounts along both virtual boundary 230 and virtual boundary 260, the effects of a virtual collision represented by overlap 270 may optionally be represented by noting where maximum overlap between virtual boundary 230 and virtual boundary 260 occurs. In some examples, collision engine 152 detects the maximum overlap by finding a point on a first one of the virtual boundaries (e.g., virtual boundary 230) that extends farthest into the region defined by a second one of the virtual boundaries (e.g., virtual boundary 260) and noting a distance between the first virtual boundary and the second virtual boundary along a direction of a surface normal for the first virtual boundary at the maximum overlap. This is shown in FIG. 2B using the double-headed arrow at overlap 270. In some examples, the direction of the surface normal may optionally be used by physics engine 154 to determine a direction of a corresponding virtual overlap force, and the amount of maximum overlap is used by physics engine 154 to determine a magnitude of the virtual overlap force (e.g., via application of a spring model for the overlap as previously discussed). In some embodiments, additional surface and/or volume interaction models may optionally be used to determine the direction and/or the magnitude of the corresponding virtual overlap force. In some examples, physics engine 154 may optionally use a deformable material model, such a gas or fluid dynamics model, for the regions within the virtual boundaries so that the volume of the overlap in combination with a coefficient of resiliency for virtual material in the regions within the first and second virtual boundaries provides a displacing force from which the virtual overlap force is derived. Examples of models generating virtual feedback forces are described in further detail in International Patent Publication No. WO 2015/120008 entitled "System and Method for Dynamic Virtual Collision Objects," which is hereby incorporated by reference in its entirety. Examination of FIG. 2b reveals that the direction of greatest risk for an actual collision is along the direction of the virtual overlap force because this is where the links and joints of the first and second repositionable arms are closest together. FIG. 2B also shows that pushing the first and second repositionable arms apart in the direction of the virtual overlap force is an efficient way to reduce and/or eliminate overlap 270. Once the virtual overlap force is determined, it may be used to apply feedback to both the first repositionable arm and the second repositionable arm as previously described.

Figure 3:
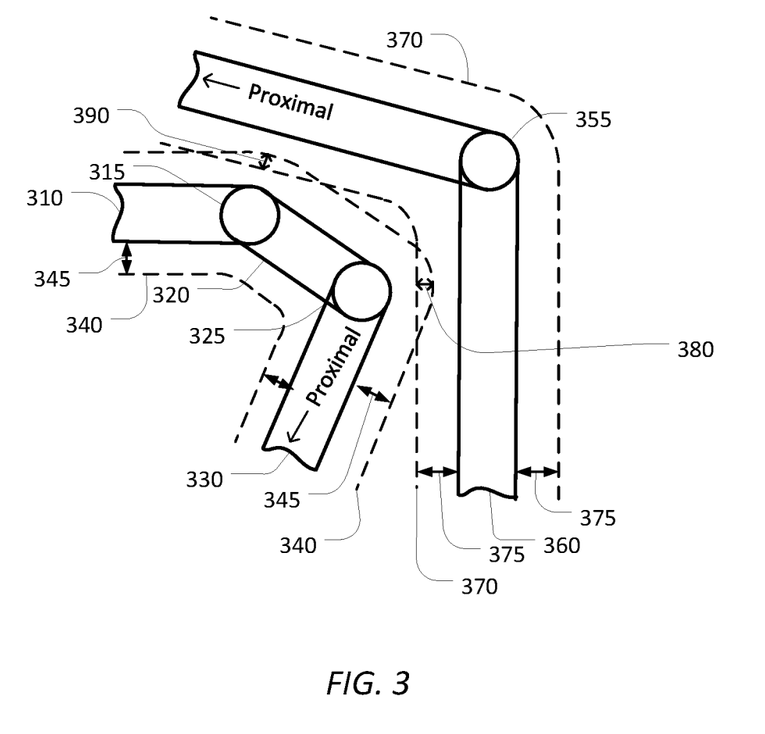
FIG. 3 is a simplified diagram of portions of two repositionable arms with virtual boundaries having multiple overlaps according to some embodiments.

FIG. 3 is a simplified diagram of portions of two repositionable arms with virtual boundaries having multiple overlaps according to some embodiments. As shown in FIG. 3, the two repositionable arms have multiple overlaps between their respective virtual boundaries. In some examples, the two repositionable arms are consistent with the repositionable arms 120 and/or end effectors 125 of device 110.

In more detail, FIG. 3 shows a portion of a first repositionable arm having links 310, 320, and 330 coupled, respectively, by joints 315 and 325. The first repositionable arm also has a virtual boundary 340 that is extended beyond the exterior surfaces of links 310, 320, and 330 and joints 315 and 325 by a predetermined distance 345. FIG. 3 also shows a portion of a second repositionable arm having links 350 and 360 coupled by a joint 355. The second repositionable arm also has a virtual boundary 370 that is extended beyond the exterior surfaces of links 350 and 360 and joint 355 by a predetermined distance 375. As with the repositionable arms and virtual boundaries of FIGS. 2A and 2B, the repositionable arms and virtual boundaries of FIG. 3 extend into three dimensions and the virtual boundaries 340 and 370 change shape as joints 315 and 325 and joint 355 are respectively manipulated.

As further shown in FIG. 3, when the first and second repositionable arms are moved closer to each other, multiple overlaps between virtual boundary 340 and virtual boundary 370 may occur, such as is depicted at overlaps 380 and 390.

Collision engine 152 and physics engine 154 initially process each of the overlaps 380 and 390 separately in much the same way they processed overlap 270. Thus, for each of overlaps 380 and 390 a respective virtual overlap force and a respective feedback to reduce and/or eliminate the respective overlap is determined independently, and it is possible that the respective feedbacks may affect different joints in both the first and second repositionable arms based on the locations of the overlaps 380 and 390. Once the respective feedbacks are separately determined, an overall composite feedback is determined using superposition. The efficacy of this superposition approach is shown in FIG. 3. For example, under the assumption that the proximal ends of the first and second repositionable arms are located as indicated by the proximal arrows in FIG. 3, feedback provided to reduce overlap 380 alone (e.g., feedback to push portions of the first and second repositionable arms apart in a mostly horizontal direction of FIG. 3, such as feedback to cause a counter-clockwise rotation of a joint (not shown) below joint 315 and a counter-clockwise rotation of joint 355) would not do much to reduce or eliminate overlap 390 and feedback provided to reduce overlap 390 alone (e.g., feedback to push portions of the first and second repositionable arms apart in a mostly vertical direction of FIG. 3, such as feedback to cause a counter-clockwise rotation of joint 325 and a counter-clockwise rotation of a joint (not shown) to the left of joint 355) would not do much to reduce or eliminate overlap 380. However, by superimposing feedback with a mostly horizontal component to reduce overlap 380 and a mostly vertical component to reduce overlap 390 is more effective at reducing and/or eliminating both overlap 380 and overlap 390. This superposition approach also generalizes to three or more points of overlap, and it is also usable to additional provide feedback that occurs due to overlaps between the first and/or second repositionable arms and a third repositionable arm (not shown).

Figure 4:
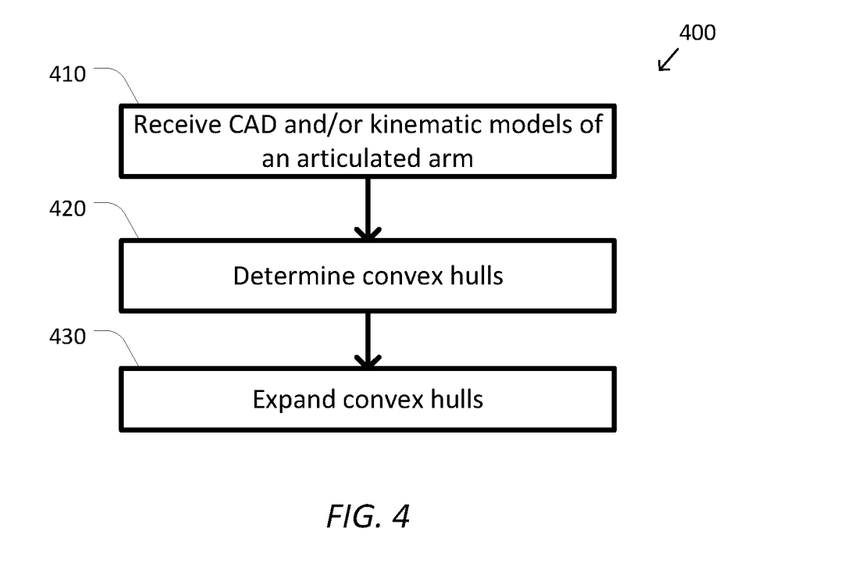
FIG. 4 is a simplified diagram of a method of generating a virtual model for a repositionable arm according to some embodiments.

FIG. 4 is a simplified diagram of a method of generating a virtual model for a repositionable arm according to some embodiments. One or more of the processes 410-430 of method 400 may be implemented, at least in part, in the form of executable code stored on non-transitory, tangible, machine readable media that when run by one or more processors (e.g., the processor 142 in control unit 130) may cause the one or more processors to perform one or more of the processes 410-430. In some embodiments, method 400 is usable to create one or more data structures and/or executable procedures to implement a corresponding model for a repositionable arm, such as any of the repositionable arms 120 and/or end effectors 125. In some embodiments, the virtual model may be one the virtual models 150. In some embodiments, method 400 is usable to create one or more virtual models for each of the repositionable arms, end effectors, and/or instruments used by a computer-assisted medical device.

At a process 410, CAD and/or kinematic models of a repositionable arm are received. The CAD and/or kinematic models should include sufficient (e.g., high fidelity) detail so that exterior surface details can be modeled with a accuracy at least as good as an accuracy to which the repositionable arm can be controlled. In some examples, high fidelity accuracy is one with an accuracy of 6-12 mm or less. Thus, the CAD and/or kinematic models include details on the types, numbers, shapes, and/or configurations of links and joints in the repositionable arm. In some examples, the CAD and/or kinematic models may further include information on how each of the joints in the repositionable arm can be manipulated and/or repositionable during operation of the repositionable arm. In some examples, the CAD and/or kinematic models may be generated from a CAD or similar tool.

At a process 420, convex hulls are determined. Using the CAD and/or kinematic models received during process 410, the repositionable arm is divided into segments. The segments are selected to that the exterior surface of each of the respective segments can be approximated within a desired accuracy using a convex hull. In some examples, a CAD tool may optionally be used to extract the convex hulls from the CAD and/or kinematic models. In some examples, the CAD and/or kinematic models may optionally include a mesh of vertices and/or control points that approximate the exterior surface of each of the respective segments. In some examples, the number of vertices and/or control points used in the mesh or as part of the convex hull model may optionally be selected based on the desired accuracy for the convex hull. In some examples, the desired accuracy is 6-12 mm or less. In some examples, the desired accuracy for each of the segments may optionally vary (e.g., so that more proximal segments of the repositionable arm are modeled with greater accuracy than more distal segments of the repositionable arm). In some examples, the convex hull determined for a respective segment may optionally represent a simplified model of the exterior surface of the respective segment by eliminating and/or smoothing out exterior surface features that have variations in dimension that are finer than the desired accuracy.

At a process 430, the convex hulls are expanded. In order to generate a virtual boundary for each of the segments, and the repositionable arm as a whole, each of the convex hulls determined during process 420 are expanded in size based on a predetermined distance. In this way, the virtual boundary provides a virtual buffer zone around the links and joints of the repositionable arm. In some examples, the predetermined distance is selected to be at least as accurate as the kinematic calibration to which a motion control module, such as motion control module 156, is able to position and orient the repositionable arm. In some examples, the predetermined distance may optionally vary for different segments of the repositionable arm. In some examples, segments located more proximally on the repositionable arm may optionally have a smaller predetermined distance than segments located more distally on the repositionable arm.

In some embodiments, the virtual model may optionally be parameterized to account for changes in the positions and/or articulations in the joints of the repositionable arm as it is operated and/or manipulated. Thus, an application or module using the virtual model is able to provide current joint positions and/or orientations to the virtual model and a corresponding virtual boundary that accounts for the current joint positions and/or orientations is generated and made available for use. In some examples, the joint positions and/or orientations are provided to the virtual model using an API and/or similar call interface.

In some embodiments, the virtual model may optionally be parameterized to designate a position along the repositionable arm at which the virtual boundary ends. In some examples, segments of the repositionable arm located distally to the position are not used to generate the virtual boundary so that the virtual boundary generated by the virtual model does not include boundary segments more distal to the position. This allows a user of the virtual model to suppress the virtual boundary more distal to the position so that overlaps and/or virtual collisions are not detected distal to the position. In some examples, this allows virtual collisions to be turned off where actual collisions between the repositionable arm and/or its end effector with another virtual arm and/or end effector are permitted. In some examples, the position is selected to correspond to where the repositionable arm and/or its end effector are inserted through a body wall of a patient. In some examples, the position may optionally correspond to a remote center of motion for the repositionable arm. In some examples, the virtual boundary may optionally be implemented using a predetermined distance of zero and/or a negative predetermined distance so that collisions are permitted, but where at least some feedback is desired to limit the severity and/or extent of the collision.

In some embodiments, method 400 is repeated to generate a virtual model for each of the repositionable arms for which collision avoidance is desired. In the examples, of FIG. 1, method 400 would be repeated for each of the repositionable arms 120 to generate a corresponding one of the virtual models in virtual models 150.

Figure 5:
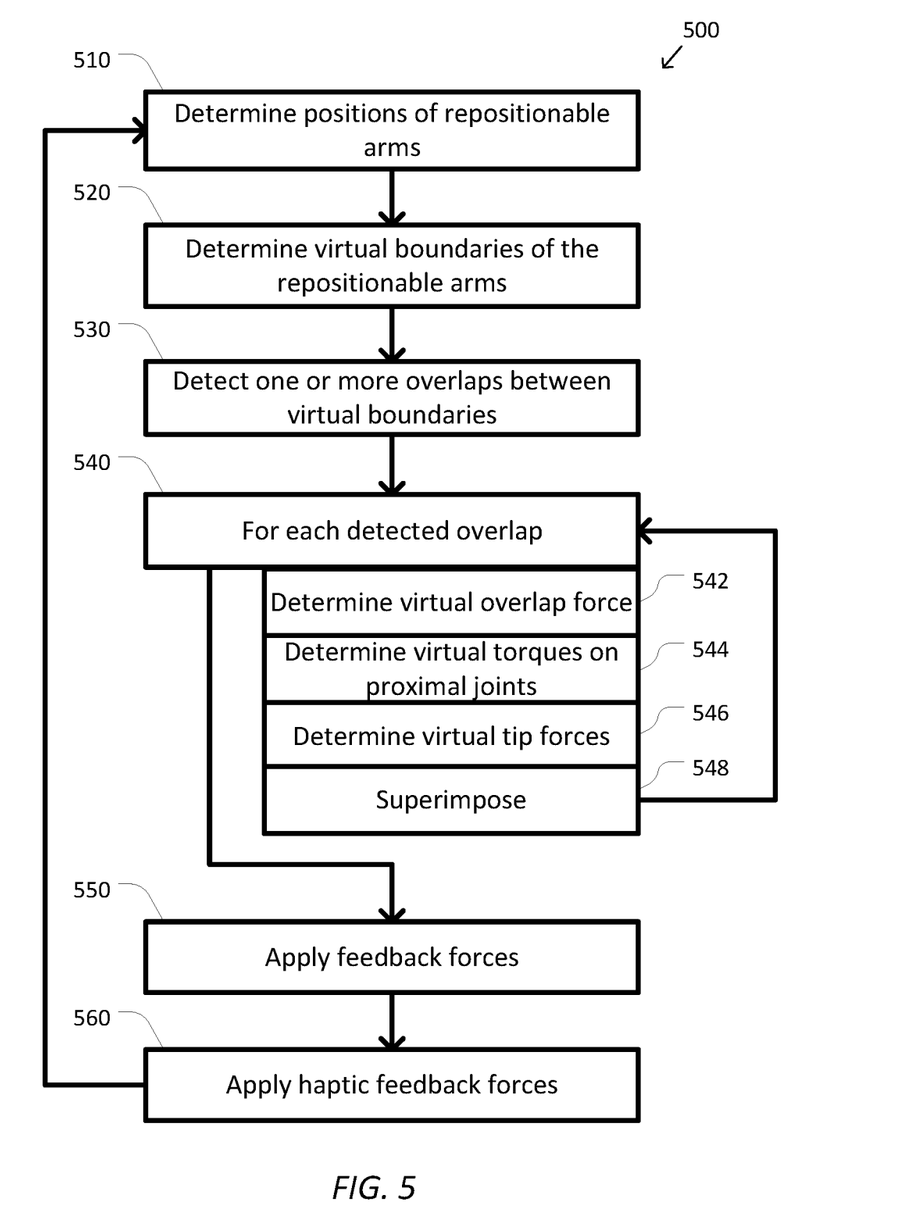
FIG. 5 is a simplified diagram of a method of collision avoidance using virtual boundaries according to some embodiments.

FIG. 5 is a simplified diagram of a method of collision avoidance using virtual boundaries according to some embodiments. One or more of the processes 510-560 of method 500 may be implemented, at least in part, in the form of executable code stored on non-transitory, tangible, machine readable media that when run by one or more processors (e.g., the processor 142 in control unit 130) may cause the one or more processors to perform one or more of the processes 510-560. In some embodiments, method 500 may optionally be performed by one or more modules or applications, such as virtual models 150, collision engine 152, physics engine 154, motion control module 156, and/or haptic feedback module 158. In some embodiments, method 500 is usable to determine one or more virtual collisions between virtual boundaries of two or more repositionable arms and use those virtual boundaries to provide feedback to the repositionable arms to help reduce and/or eliminate actual collisions between the repositionable arms. In some embodiments, method 500 is usable to provide haptic feedback to an operator of the repositionable arms to resist attempts by the operator to manipulate the repositionable arms into a configuration where an actual collision between the repositionable arms occurs. In some embodiments, method 500 is usable reduce the likelihood of collisions between repositionable arms 120 and/or end effectors 125 as they are being teleoperated using input controls 195. In some embodiments, method 500 is usable to reduce the likelihood of collisions between the repositionable arms, end effectors, and/or instruments of a computer-assisted medical device while the computer-assisted medical device is being used to perform one or more procedures.

At a process 510, positions of the repositionable arms are determined. Collision avoidance between repositionable arms and/or their end effectors begins by determining current positions of each of the repositionable arms and/or their end effectors for which collision avoidance is desired. In some embodiments, data from one or more sensors associated with joints of each of the repositionable arms is received. The sensor data includes information on the orientation of the joints in the repositionable arms so that the current position of the repositionable arms is determined. In some examples, one or more kinematic models and/or virtual modules, such as the virtual models generated using method 400, are used to convert the joint orientation information into positions of the repositionable arms. In some examples, the orientations of the joints are provided as parameters to the one or more kinematic and/or virtual models. In some embodiments, one or more registration markers, fiducial markers, and/or the like mounted on the repositionable arms may alternatively be tracked using one or more tracking sensors, such as an imaging device, to supplement and/or replace the sensor data to determine the orientations of the joints in the repositionable arms.

At a process 520, virtual boundaries of the repositionable arms are determined. Once the positions of the repositionable arms are determined during process 510, the positions of the repositionable arms are usable to generate current positions of the virtual boundaries of each of the repositionable arms using the one or more virtual models. In some examples, the one or more virtual modules correspond to the virtual models 150 and/or the virtual models generated using method 400.

At a process 530, one or more overlaps between the virtual boundaries are determined. The virtual boundaries determined for each repositionable arm during process 520 are compared using a collision engine, such as collision engine 152, to determine whether there are any overlaps between the virtual boundaries of different repositionable arms. In some examples, because each of the virtual boundaries may optionally be defined using one or more convex objects, such as the convex hulls determined during process 430, each of the convex objects from each virtual boundary are compared against the convex objects for each of the other virtual boundaries in order to find each place where an overlap in virtual boundaries occurs. In some examples, the comparison may optionally include an iterative comparison strategy where a coarse approximation of the convex objects is used to quickly determine potential overlaps and the actual models of the convex objects and the virtual boundaries is used to detect the actual overlaps. In some examples, an overlap between two virtual boundaries is detected whenever one of the virtual boundaries intrudes into or intersects the other virtual boundary. In some examples, detection of each overlap includes determining an amount and location of maximum overlap between the two virtual boundaries as well as a direction of the maximum overlap and/or other virtual overlap properties from which a direction and magnitude of a virtual overlap force may be determined. In some examples, the maximum overlap is determined by finding a point on a first one of the virtual boundaries that extends furthest into the region defined by a second one of the virtual boundaries and noting a distance between the first virtual boundary and the second virtual boundary along a direction of a surface normal for the first virtual boundary at the maximum overlap. In some examples, the direction of the surface normal is used to determine a direction associated with the overlap that indicates a direction to which a feedback force should be applied to reduce and/or eliminate the overlap.

At a process 540, each of the overlaps detected during process 530 are processed in turn so that the effects of each of the overlaps and their corresponding virtual collision is used to provide feedback to reduce and/or eliminate the virtual collisions. As each overlap is processed it becomes the current overlap.

At a process 542, a virtual overlap force for the current overlap is determined. The current overlap detected during process 530 is processed by a physics engine, such as physics engine 154, to determine a virtual overlap force of the current virtual collision. In some examples, a magnitude of the virtual overlap force is based on an amount of overlap and a direction of the virtual overlap force is based on a direction of the maximum overlap between the virtual boundaries and/or based on a surface normal of the virtual boundaries at the overlap. In some examples, a virtual spring model with a linear or alternatively a non-linear constant is used to determine the magnitude of the virtual overlap force. In some examples a deformable material model, such a gas or fluid dynamics model, for the regions within the virtual boundaries so that the volume of the overlap in combination with a coefficient of resiliency for virtual material in the regions within the virtual boundaries provides a displacing force from which the virtual overlap force is derived. Examples of models generating virtual feedback forces are described in further detail in International Patent Publication No. WO 2015/120008 entitled "System and Method for Dynamic Virtual Collision Objects," which is hereby incorporated by reference in its entirety.

At a process 544, virtual torques on proximal joints are determined. Using the virtual overlap force determined during process 542, a corresponding virtual torque in each joint proximal to the overlap in both repositionable arms associated with the current virtual collision are determined. In some examples, a respective Jacobian transpose between the point of overlap and the proximal joints is used to map the virtual overlap force to the virtual torques. In this embodiment, computation of the virtual torques is limited to those joints proximal to the overlap as the overlap can be satisfactorily reduced and/or eliminated using only joints proximal to the point of the virtual collision; in other embodiments, computation of the virtual torques are determined for other joints as well In some examples, the kinematics of the repositionable arm may sometimes result in no virtual torque being computed for one or more of the joints proximal to the overlap indicating that manipulation of those joints does not contribute to the reduction or elimination of the overlap. Virtual torques are determined separately for each of the repositionable arms associated with the current virtual collision as the current virtual collision can occur at different locations on the two repositionable arms and the two repositionable arms can have different kinematic models. In some examples, the determination of the virtual torques on the proximal joints may optionally be performed by either the physics engine and/or the motion control module.

At a process 546, virtual tip forces are determined. Using the virtual torques determined during process 544, a corresponding virtual tip force for each of the repositionable arms associated with the current virtual collisions is determined. Each corresponding virtual tip force represents an effective force that can be applied to the distal-most end of the corresponding repositionable arm to move the repositionable arm away from the current overlap. In some examples, the virtual torques for each repositionable arm are mapped to the corresponding virtual tip force using an inverse of a corresponding Jacobian transpose between the distal-most end of the corresponding repositionable arm and the joints of the corresponding repositionable arm.

At a process 548, the effects of the current overlap are superimposed with the effects of previously processed overlaps. In some examples, the virtual tip force determined during process 546 for each of the repositionable arms is superimposed (e.g., added to) any previous virtual tip force determined for the corresponding repositionable arms. Thus, at process 548 the virtual tip force is adjusted with each current overlap and corresponding current virtual collision that the corresponding repositionable arm is subject to, to generate an overall virtual tip force for each of the repositionable arms. In some examples, the superposition of the effects of the overlaps may optionally be performed by either the physics engine and/or the motion control module.

Processes 542-548 are then repeated for each of the overlaps detected during process 530.

At a process 550, feedback forces are applied. The overall virtual tip forces generated during process 548 are applied as a feedback force to each of the repositionable arms. In some examples, the overall virtual tip force for each of the repositionable arms is provided to a motion control application, such as a motion control application comprising a motion control module (e.g., motion control module 156), for the corresponding repositionable arm. The motion control application applies the overall virtual tip force as a feedback to the motion control of the corresponding repositionable arm so that the corresponding repositionable arm opposes the virtual collisions detected for the corresponding repositionable arm. In this way, motion control module is able to apply a resisting effect that helps prevent the corresponding repositionable arm from being teleoperated closer to an actual collision, but does not oppose motion that moves the corresponding repositionable arm from an impending collision. In some examples, the feedback of the corresponding virtual tip force is superimposed on the motion dictated by the teleoperated commands for the corresponding repositionable arm.

At a process 560, haptic feedback forces are applied. The overall tip forces generated during process 548 are applied as haptic feedback to corresponding input controls, such as input controls 195, used to teleoperate the corresponding repositionable arms. In some examples, each of the overall tip forces is scaled to reflect differences in relative force used to manipulate the corresponding repositionable arm and the force used to manipulate the corresponding input control. In some examples, an inverse of a Jacobian transpose for the corresponding input control is used to map the overall tip force to respective joint torques in the repositionable arm of the input control to apply haptic feedback to the corresponding input control. In some embodiments, differences between actual positions of the corresponding repositionable arm and a commanded position of the corresponding repositionable arm are optionally used to determine the haptic feedback on the corresponding input control. In some embodiments, differences between a current command to the corresponding repositionable arm as adjusted by the feedback forces applied during process 550 and a commanded position of the corresponding repositionable arm from the corresponding input control are optionally used to determine the haptic feedback on the corresponding input control.

Processes 510-560 are then repeated at suitable intervals, such as during a control loop for a device having the repositionable arms, to provide continuous monitoring of overlaps between the virtual boundaries that indicate virtual collisions and to provide feedback to the repositionable arms and haptic feedback to the input controls.

As discussed above and further emphasized here, FIG. 5 is merely an example which should not unduly limit the scope of the claims. One of ordinary skill in the art would recognize many variations, alternatives, and modifications. In some embodiments, when no overlaps are detected during process 530, processes 540-560 are skipped and no feedback forces and/or haptic feedback forces are applied. In some embodiments, the effects of each of the overlaps may optionally be superimposed in different ways. In some examples, the virtual torques determined during process 544 may be superimposed on a joint-by-joint basis to determine an overall virtual torque for each of the joints in the repositionable arms due to the overlaps and corresponding virtual collisions detected during process 530. The overall virtual torques are then provided to the motion control application where they are superimposed on the joint torques due to other control inputs, such as the teleoperation commands from the input controls.

In some embodiments, the effects due to redundant degrees of freedom in the repositionable arms may optionally be accounted for when applying the feedback and/or haptic feedback forces. Because a repositionable arm with redundant degrees of freedom in its motion may include repositionable element and/or joint motions that do not affect the pose of the tip of the repositionable arm, motions of a repositionable arm are dividable into two orthogonal sets of motion: those that result in a change in the pose of the tip and those that do not result in a change in the pose of the tip and are sometimes referred to as null space motions. To address this, feedback forces applied to the repositionable elements and/or joints of the repositionable arm that are null space motions may optionally be omitted as they do not result in motion of the tip and consequently do not generate haptic feedback motion.

In some embodiments, it may be desirable to slowly phase in the feedback effects of method 500. In some examples, a transition of an operating mode of a computer-assisted medical device from a mode where method 500 is not used and a mode where method 500 is used may result in an undesirable risk of end effector and/or repositionable arm motion. In some examples, when there is a pre-existing overlap between two repositionable arms when the transition between mode occurs, the rapid application of the feedback forces during process 550 and/or haptic feedback forces during process 560 when no such forces were previously applied, this may result in unexpected and/or undesirable motion in the end effectors and/or repositionable arms. In some examples, this may optionally be addressed by phasing in the feedback and haptic feedback forces upon initial transition into the mode where method 500 is performed. In some examples, the feedback forces and/or the haptic feedback forces may optionally be phased in using ramps, a sequence of steps, and/or the like. In some examples, the feedback forces and/or haptic forces may optionally be phased in over a predetermined period of time, such as approximately one second.

Some examples of control units, such as control unit 130 may include non-transitory, tangible, machine readable media that include executable code that when run by one or more processors (e.g., processor 142) may cause the one or more processors to perform the processes of methods 400 and/or 500. Some common forms of machine readable media that may include the processes of methods 400 and/or 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. For example, an analogous technique can be applied to determine one or more other virtual boundaries around other objects other than repositionable arms, end effectors, or arm-and-end-effector assemblies. Such other objects can include another part of device 110, a part of operator workstation 170, other equipment such as operating beds, carts, furniture, walls, people, etc. The process used to detect and respond to virtual collisions by a repositionable arm, end effector, or arm-and-end-effector assembly with such other virtual boundary can be the same for such virtually colliding arm, end effector, or arm-and-end-effector assembly as described herein.

Thus, the scope of the invention should be limited only by the following claims, and it is appropriate that the claims be construed broadly and in a manner consistent with the scope of the embodiments disclosed herein.

What is claimed is:

1. A computer-assisted device comprising:
  a repositionable arm configured to support an instrument; and
  a control unit comprising one or more processors, the control unit being coupled to the repositionable arm, wherein the control unit is configured to:
    determine a position and an orientation, the position and the orientation being of the repositionable arm or of the instrument;
    determine, based on the position and the orientation, a plurality of first virtual boundaries around the repositionable arm or the instrument;
    determine a second virtual boundary around an object;
    determine a tip force on a distal end of the instrument based on a first overlap between the second virtual boundary and a virtual boundary of the plurality of first virtual boundaries; and
    apply the tip force as a first feedback force on the instrument or the repositionable arm.

2. The computer-assisted device of claim 1, wherein to determine the tip force based on the first overlap, the control unit is configured to:
  map a first overlap force to a virtual torque on a joint of the repositionable arm; and
  determine the tip force based on the virtual torque.

3. The computer-assisted device of claim 1, wherein to determine the position and the orientation the control unit is configured to:
  determine a joint position for each of one or more joints of the repositionable arm; and
  determine the position and the orientation from each joint position.

4. The computer-assisted device of claim 1, wherein the control unit is further configured to:
  apply haptic feedback to an input control based on the tip force, the control unit being configured to receive movement commands for the instrument from the input control.

5. The computer-assisted device of claim 4, wherein the control unit is further configured to determine the haptic feedback based on a difference between a first commanded position of the instrument due to application of the first feedback force on the instrument and a second commanded position of the instrument determined from the input control.

6. The computer-assisted device of claim 1, wherein to determine the tip force on the distal end of the instrument the control unit is configured to:
  determine an overlap force on the repositionable arm due to the first overlap between the second virtual boundary and a virtual boundary of the plurality of first virtual boundaries; and
  determine the tip force on the distal end of the instrument based on the overlap force.

7. The computer-assisted device of claim 1, wherein the plurality of first virtual boundaries comprises a plurality of convex hulls that approximates a physical geometry of the repositionable arm.

8. The computer-assisted device of claim 1, wherein the plurality of first virtual boundaries are determined only for portions of the repositionable arm or the instrument proximal to a body opening or a remote center of motion, wherein the instrument is inserted into the body opening, and wherein the remote center of motion is of the repositionable arm or the instrument.

9. The computer-assisted device of claim 6, wherein a magnitude of the overlap force is determined based on a maximum overlap of the first overlap, a surface area of the first overlap, or a volume of the first overlap.

10. The computer-assisted device of claim 1, wherein the first feedback force is superimposed on forces applied to the instrument as a result of movement commands received from an input control.

11. The computer-assisted device of claim 1, wherein the first feedback force opposes motion of the repositionable arm that is likely to cause a collision between the repositionable arm and the object.

12. A method of collision avoidance, the method comprising:
   determining, by a control unit, a position and an orientation, the position and the orientation being of a repositionable arm or of an instrument, the repositionable arm being configured to support the instrument;
   determining, by the control unit based on the position and the orientation, a plurality of first virtual boundaries around the repositionable arm or the instrument;
   determining, by the control unit, a second virtual boundary around an object;
   determining, by the control unit, a tip force on a distal end of the instrument based on a first overlap between the second virtual boundary and a virtual boundary of the plurality of first virtual boundaries; and
   applying, by the control unit, the tip force as a first feedback force on the instrument or the repositionable arm.

13. The method of claim 12, wherein determining the tip force based on the first overlap comprises:
   mapping a first overlap force to a virtual torque on a joint of the repositionable arm; and
   determining the tip force based on the virtual torque.

14. The method of claim 12, wherein determining the position and the orientation comprises:
   determining a joint position for each of one or more joints of the repositionable arm; and
   determining the position and the orientation from each joint position.

15. The method of claim 12, further comprising:
   applying, by the control unit, haptic feedback to an input control based on the tip force, the control unit being configured to receive movement commands for the instrument from the input control.

16. The method of claim 12, further comprising:
   determining, by the control unit, an overlap force on the repositionable arm due to a second overlap between a second one the plurality of first virtual boundaries and a virtual boundary of another repositionable arm;
   determining, by the control unit, a second tip force on the distal end of the instrument based on the overlap force; and
   applying, by the control unit, the second tip force as a second feedback force on the instrument or the repositionable arm.

17. A non-transitory machine-readable medium comprising a plurality of machine-readable instructions which when executed by one or more processors are adapted to cause the one or more processors to perform a method comprising:
   determining a position and an orientation, the position and the orientation being of a repositionable arm or of an instrument, the repositionable arm being configured to support the instrument;
   determining, based on the position and the orientation, a plurality of first virtual boundaries around the repositionable arm or the instrument;
   determining a second virtual boundary around an object;
   determining a tip force on a distal end of the instrument based on a first overlap between the second virtual boundary and a virtual boundary of the plurality of first virtual boundaries; and
   applying the tip force as a first feedback force on the instrument or the repositionable arm.

18. The non-transitory machine-readable medium of claim 17, wherein determining the tip force based on the first overlap comprises:
   mapping a first overlap force to a virtual torque on a joint of the repositionable arm; and
   determining the tip force based on the virtual torque.

19. The non-transitory machine-readable medium of claim 17, wherein determining the position and the orientation comprises:
   determining a joint position for each of one or more joints of the repositionable arm; and
   determining the position and the orientation from each joint position.

20. The non-transitory machine-readable medium of claim 17, wherein:
   the method further comprises applying haptic feedback to an input control based on the tip force; and
   movement commands for the instrument are received from the input control.

* * * * *

UNITED STATES PATENT AND TRADEMARK OFFICE
CERTIFICATE OF CORRECTION

| | |
|---|---|
| PATENT NO. | : 11,485,016 B2 |
| APPLICATION NO. | : 16/896083 |
| DATED | : November 1, 2022 |
| INVENTOR(S) | : Paul G. Griffiths and Nitish Swarup |

It is certified that error appears in the above-identified patent and that said Letters Patent is hereby corrected as shown below:

On the Title Page

(63) Related U.S. Application Data:
Please delete "Continuation of application No. 16/079,970, filed as application No. PCT/US2017/016427 on Feb. 3, 2017, now Pat. No. 10,717,194." and insert --Continuation of application No. 16/079,970, filed on Aug. 24, 2018, now Pat. No. 10,717,194, which is a 371 of application No. PCT/US2017/016427, filed on Feb. 3, 2017.--.

Signed and Sealed this
Twentieth Day of December, 2022

*Katherine Kelly Vidal*

Katherine Kelly Vidal
*Director of the United States Patent and Trademark Office*